(12) United States Patent
Angelucci et al.

(10) Patent No.: US 6,328,953 B1
(45) Date of Patent: Dec. 11, 2001

(54) POLYMERIC DERIVATIVES OF CAMPTOTHECINS

(75) Inventors: Francesco Angelucci; Fabrizio Orzi, both of Milan; Gabriele Fachin, Cilavegna-Pavia; Valeria Caiolfa, Milan; Moreno Zamai, Milan; Antonino Suarato, Milan, all of (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 09/509,534

(22) PCT Filed: Sep. 22, 1998

(86) PCT No.: PCT/EP98/06048

§ 371 Date: Mar. 31, 2000

§ 102(e) Date: Mar. 31, 2000

(87) PCT Pub. No.: WO99/17804

PCT Pub. Date: Apr. 15, 1999

(30) Foreign Application Priority Data

Oct. 3, 1997 (GB) .................................. 9721069

(51) Int. Cl.$^7$ ........................ A61K 31/435; C07D 491/22
(52) U.S. Cl. .................................... 424/78.29; 424/78.32; 546/48; 525/329.4; 514/81
(58) Field of Search ........................... 546/48; 424/78.32, 424/78.29

(56) References Cited

U.S. PATENT DOCUMENTS

| | | | |
|---|---|---|---|
| 5,362,831 | 11/1994 | Mongelli et al. | 526/304 |
| 5,473,055 | 12/1995 | Mongelli et al. | 530/329 |
| 5,569,720 | 10/1996 | Mongelli et al. | 525/329.4 |
| 5,571,785 | 11/1996 | Angelucci et al. | 514/8 |
| 5,719,265 | 2/1998 | Mongelli et al. | 530/329 |
| 5,773,522 * | 6/1998 | Angelucci et al. | 525/329.4 |

* cited by examiner

*Primary Examiner*—Bernard Dentz
(74) *Attorney, Agent, or Firm*—Oblon, Spivak, McClelland, Maier & Neustadt, P.C.

(57) ABSTRACT

The invention relates to polymeric conjugates of 20-O-[glycyl-aminoacyl-glycyl]-camptothecins and a process for producing the same.

17 Claims, No Drawings

POLYMERIC DERIVATIVES OF CAMPTOTHECINS

This application is a 371 of PCT/EP98/06048 filed Sep. 22, 1998.

The invention relates to polymeric conjugates of 20-O-[glycyl-aminoacyl-glycyl]camptothecins. Our WO-95/10304 describes and claims conjugates of camptothecins linked to a polymer through a peptidyl spacer. We have now found that the conjugates in which the spacer is a glycyl-aminoacyl-glycyl are of exceptional value as antitumor agent and are endowed with remarkable antitumor activity and reduced toxicity in comparison with the free drug.

Particularly the present invention provides polymeric conjugates of the formula (1) consisting of:

(i) from 85 to 97 mol % of N-(2-hydroxypropyl) methacryloylamide units represented by formula (3)

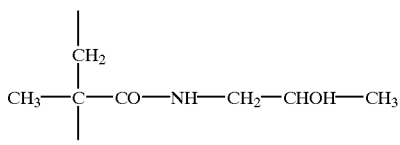

(3)

(ii) from 3 to 15 mol % of 20-O-(N-methacryloyl-glycyl-aminoacyl-glycyl)-camptothecin units represented by formula (4).

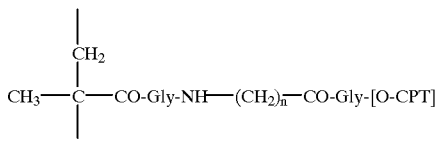

(4)

wherein n is from 2 to 8, —[O-CPT] represents the residue of a camptothecin of formula (2)

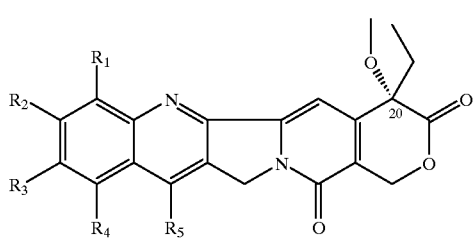

(2)

which is linked at the C-20 position and in which each of $R_1$, $R_2$, $R_3$, $R_4$ and $R_5$ which are the same or different, is hydrogen, $C_1$–$C_{12}$ linear or branched alkyl, nitro, amino, $(CH_2)_aNR_6R_7$ in which a is from 0 to 4 and $R_6$ and $R_7$ are hydrogen or one of $R_6$ or $R_7$ is hydrogen and the other of $R_6$ or $R_7$ is $C_1$–$C_6$ alkyl, or $NR_6R_7$ represents a piperazino or N-alkyl-piperazino ring optionally substituted with $C_1$–$C_6$ linear or branched alkyl or piperidino ring, $(CH_2)_aNHCOR_8$ in which a is as above defined and $R_8$ is $C_1$–$C_8$ linear or branched alkyl or a group $NR_6R_7$ as above, hydroxy or $O$-$CO$-$R_8$ in which $R_8$ is as above defined or represents a 1-piperidino ring or 1,4'-bipiperidine, or $R_2$ and $R_3$ taken together represent the residue $O$—$(CH_2)_b$—$O$, in which b is 1 or 2, or $R_4$ and $R_5$ represent the residue $(CH_2)_m$, in which m is from 2 to 4, or the residue $CH_2$—$O$—$CH_2$ or $CH_2NHCH_2$ and (iii) from 0 to 12 mol % of N-methacryloyl-glycine or N-(2-hydroxy-propyl)methacryloyl-glycinamide units represented by formula (5)

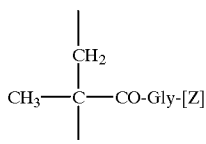

(5)

wherein [Z] represents a hydroxy group or a residue of formula —NH—$CH_2$—CH(OH)—$CH_3$.

The polymeric conjugates of the formula (1) may be indicated as MAG-CPT(s) and may also be represented as follows:

$[(3)]_x$; $[(4)]_y$; $[(5)]_z$ wherein (3), (4) and (5) are units of the formula as above defined, and x is from 85 to 97 mol %, y is from 3 to 15 mol % and z is from 0 to 12 mol %.

A preferred embodiment of compounds of the present invention are those in which —[O-CPT] in formula (4) is a residue of a camptothecin of formula (2) selected from:

camptothecin [2a: $R_1=R_2=R_3=R_4=R_5=H$];

9-aminocamptothecin [2b: $R_1=R_2=R_3=R_5=H$, $R_4=NH_2$];

9-nitrocamptothecin [2c: $R_1=R_2=R_3=R_5=H$, $R_4=NO_2$];

7-ethyl-10-hydroxycamptothecin [2d: $R_1=R_2=R_4=H$, $R_3=OH$, $R_5=CH_2CH_3$];

7-ethyl-10-[1,4'-bipiperidinyl]carbonyloxycamptothecin [2e: $R_1=R_2=R_4=H$, $R_3=OCO$-[1,4'-bipiperidinyl], $R_5=CH_2CH_3$], 7-methylendimethylamino-10-hydroxycamptothecin [2f: $R_1=R_2=R_4=H$, $R_3=OH$, $R_5=CH_2N(CH_3)_2$] and 7-[methylen-(4'-methylpiperazino)]-9,10-ethylendioxycamptothecin [2g: $R_1=R_4=H$, $R_2,R_3=O$—$CH_2CH_2$—$O$, $R_5$=methylen-(4'-methylpiperazino)].

Preferably, the polymeric conjugates of the formula (1) contain the N-(2-hydroxypropyl) methacryloyl amide units represented by the formula (3) in a proportion of 90% or more; more preferably 90%. The conjugate may also contain from 3 to 10 mol % of the units represented by the formula (4), more preferably 10 mol % of such units. Preferably the conjugate of formula (1) does not contain residues of formula (5), i.e. z is 0. Content of active camptothecin derivative of formula (2) in the conjugate of formula (1) may be from 2 to 15% (weight/weight), more preferably 10% (w/w). The preparation of the compounds of the present invention may be carried out by a process (herein named Route I) which comprises reacting 20-O-(aminoacyl-glycyl) camptothecin derivative of formula (6)

$NH_2$—$(CH_2)_n$—CO-Gly-[OCPT]  (6)

wherein n and [OCPT] are as above defined, with a polymer (B) consisting essentially of:

from 85 to 97 mol % of N-(2-hydroxypropyl) methacryloylamide units represented by formula (3) as above defined, and from 3 to 15 mol % of N-methacryloyl-glycyl derivative units represented by formula (7)

(7)

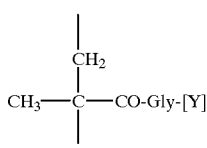

wherein [Y] is the residue of an active ester, preferably p-nitrophenyl ester, or a hydroxy group; and optionally displacing the remaining active ester groups with 1-amino-2-propanol. The condensation of derivative of formula (6) with the polymer of formula (B), is carried out in conditions capable of preserving the nature of linkage between camptothecin and the aminoacyl-glycyl spacer as well as that of the conjugate.

Polymers of formula (B), consisting of N-(2-hydroxypropyl)-methacryloylamide units of formula (3) and of N-methacryloyl-glycine units of formula (7), are prepared by copolymerization of N-(2-hydroxypropyl) methacrylamide with N-methacryloyl-glycine or N-methacryloyl-glycine active-ester derivatives, as described in Makromol.Chem. 178, 2159 (1977). The residue [Y] may represent a phenoxy group which is substituted on the phenyl ring by one ore more electron-withdrawing groups, such as nitro or halogen. Preferably the residue [Y] represents p-nitro phenoxy.

Reaction between (6) and (B) to form polymeric-drug-conjugate of formula (1) of the present invention can typically carried out at temperature from 15 to 30° C., preferably at room temperature for 15 hours; then the aminolysis of the remaining active ester groups can be performed in the presence of 1-amino-2-propanol at room temperature, from 0.5 to 1 hour. The conjugate suitably is precipitate with ethyl acetate dissolved in ethanol and reprecipitated with ethyl acetate.

For example, the polymer (B) in which [Y] represents the residue of an active ester, provided at a concentration of 15% (weight/volume) in dry dimethylsulfoxide, is treated with 20-O-(aminoacyl-glycyl)camptothecin derivative (6), 3% (w/v), at room temperature for 15 hours. Then 1-amino-2-propanol, 0.1% (w/v) is added and the reaction mixture is kept at room temperature for 1 hour. The polymeric-drug-conjugate. MAG-CPTs, can be precipitated with ethyl acetate, collected, washed with ethyl acetate, then dissolved with absolute ethanol at a concentration of 10% (weight/volume) and precipitated again with ethyl acetate to give the conjugates of formula (1) according to the invention. The content of camptothecin in the polymeric conjugate of the invention is determined by HPLC or absorbance spectroscopy analysis.

The compounds of the formula (1) c an be also prepared by a process (herein named Route II) which comprises the polymerization between N-(2-hydroxypropyl) methacrylamide of the formula (8)

(8)

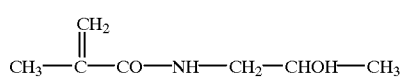

and 20-O-[methacryloyl-glycyl-(aminoacyl )-glycyl] camptothecin derivatives of the formula (9)

(9)

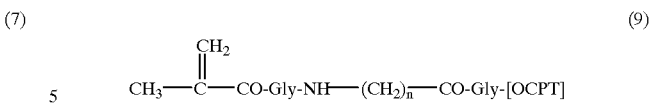

wherein n and [OCPT] are as above defined, in conditions capable of preserving the nature of linkage between camptothecin and spacer glycyl-aminoacyl-glycyl as well as that of the conjugate.

Reaction between (8) and (9) can typically carried out at temperature from 50 to 70° C., preferably at 60° C., from 6 to 24 hours, preferably for 15 hours, in aprotic solvent such as dimethylsulfoxide and in presence of catalyst, such as 2,2'-azobisisobutyronitrile. The conjugate is precipitate with ethyl acetate dissolved in ethanol and reprecipitated with ethyl acetate.

For example N-(2-hydroxypropyl)methacrylamide (8), provided at a concentration of 22% (w/v) and 20-O-[methacryloyl-glycyl-(6-aminohexanoyl)-glycyl] camptothecin derivative (9) at concentration of 6% (w/v) in dry dimethylsulfoxide are heated at 60° C. under nitrogen and then added with 2,2'-azobisisobutyronitrile at concentration of 1.3% (w/v). The mixture is kept under stirring for 24 hours. After that, the reaction mixture is cooled at room temperature and the conjugate suitably is precipitate with ethyl acetate, dissolved in ethanol and reprecipitated with ethyl acetate to give conjugate of formula (1) according to the invention.

The invention also provides 20-O-acylamino-glycyl-camptothecin derivatives (6) as defined above and their salt derivatives.

The present invention further provides a process for preparing 20-O-(aminoacyl-glycyl) camptothecin derivatives (6), which process comprises condensing the residue of the formula (2) as defined above with a N-protected aminoacyl-glycyl derivative of formula (10):

R$_9$—HN—(CH$_2$)$_n$—CO-Gly-[P]  (10)

wherein n is as above defined, R$_9$ represents an amino-protecting group such as Boc, FMOC, triphenylsilyl, diphenylmethylene or triphenylmethyl, and [P] is a residue of an activated ester, such as p-nitro phenoxy or N-hydroxysuccinimido to give a compound represented by formula (11):

R$_9$—NH—(CH$_2$)$_n$—CO-Gly-[OCPT]  (11)

wherein n, [OCPT] and R$_9$ are as defined above; and removing the N-protecting group from the resulting compound.

Preparation of compounds of formula (10) follows standard synthetic procedures that are known from the literature. Suitable N-protected-aminoacyl derivatives of formula (10) include: 6-N-(triphenylmethyl)hexanonyl glycyl p-nitrophenylester (10a), 6-N-(tert-Butoxy carbonyl) hexanonyl-glycyl p-nitrophenyl ester (10b).

Thus, for example, camptothecin (2a) may be allowed to react with a molar excess, for example up to five-fold molar excess or more, especially 2 mol.equivalent, of a N-protected-aminoacyl derivative of formula 10 in anhydrous solvent such as dry dimethylsulfoxide in the presence of 4-dimethylaminopyridine.

The reaction can typically be effected for from 8 to 48 hours. The reaction is typically carried out at a temperature from 15 to 40° C. The temporary amino-protected group R$_9$ is removed by an appropriate deprotecting agent to give the 20-O-(aminoacyl-glycyl)camptothecin of formula (6a). Deprotection may be therefore achieved by acid treatment, such as treatment with 1.5N aqueous hydrochloric acid in acetic acid or 90% aqueous trifluoroacetic acid from one to 6 hours at temperature from 10 to 30° C.; preferably for two hours at room temperature.

The invention also provides 20-O-[methacryloyl-glycyl-(aminoacyl)-glycyl]camptothecin derivatives (9) as above defined and a process for their preparation, which comprises condensing camptothecin derivatives of formula (6) as above defined with N-methacryloyl-glycyl of formula (7'),

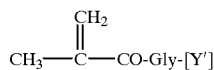

(7')

wherein [Y'] is a leaving group. Thus, for example, 20-O-[aminoacyl-glycyl]camptothecin (6a), provided at a concentration of 25% (w/v) in dry dimethyl sulfoxide, is reacted with of N-(methacryloyl-glycyl) p-nitrophenyl ester ((7'), [Y']=p-nitro-phenol), 13% (w/v) in presence of equivalent amount of base, such as triethylamine, for 15 at room temperature. The final derivative is isolated by precipitation and purified by chromatography. The compounds of the formula (8) and the polymer (B) are known or may be prepared by known synthetic methods.

All the camptothecin derivatives of formula (2) are known, see for example Medicinal Research Reviews, Vol 17, No.4, 367–425, 1997, or may be prepared by means of well known perocedures.

The polymer-bound conjugates of formula (1) are in the range of 5,000 to 45,000 molecular weight, preferably from 8,000 to 35,000. Polymeric drug conjugates of formula (1) are water soluble and show remarkable antitumor activity and reduced toxicity in comparison with the free camptothecin.

Antitumor Activity

Campound A1 was tested on human colon carcinoma (HT29) transplanted in nude mice, in comparison with the free drug (2a) by i.v. route. A1 was found non toxic and gave >95% tumor inhibition at all tested doses with an exceptional high number of tumor free animals at the end of the experiment (90 days), Table 1. Also compound A2, tested on the same model in comparison with free 7-ethyl-10-hydroxycamptothecin (2d), was found active and not toxic and gave 98% tumor inhibition at the highest tested dose of 40 mg/kg (Table 2). Compound A1 was also tested by i.v. route on a broad panel of other human tumor models: A2780 ovary ca., MX1 mammary ca., A549 NSC lung ca. and M14 melanoma. Compound A1 was more active respect to the corresponding free camptothecin (2a) and gave a large number of cured animals.

Activity against MX1 mammary carcinoma, A2780 ovary carcinoma and M14 melanoma, in comparison with free camptothecin, are reported respectively in Table 3, 4 and 5. Compound A1 was very active against these tumor models for which total inhibition of tumor growth was observed with total 7/7 and 8/8 cured mice upon repeated i.v. administration of the drug either at 15 or 20 mg/kg at the schedule of q4dx6. Compound A1 was found also active against NSC lung carcinoma at 20 mg/kg (iv q4dx6) with TI % 94 and with remarkable tumor growth dalay of 70 days never observed with other useful chemotherapeutic agents (Table 6).

TABLE 1

Antitumor Activity of A1 on human colon carcinoma (HT29) in comparison with (2a). Treatment iv q4dx6.

| Compound | Dose mg/kg | Total Dose mg/kg | TI % 37$^{th}$ day | Tox | Tumor Free | ΔTGD (0.5 g) days |
|---|---|---|---|---|---|---|
| A1 | 15 | 90 | 97 | 0/7 | 2/7 | >88 |
|  | 17.5 | 105 | 98 | 0/7 | 1/7 | >88 |
|  | 20 | 120 | 99 | 0/7 | 5/7 | >88 |
|  | 22.5 | 135 | 99 | 0/7 | 6/7 | >88 |
| 2a | 12.5 | 75 | 94 | 0/7 | 0/7 | 43 |

Tumor fragment were implanted sc. Treatment started when tumor was palpable.

TI % (tumor inhibition %) was calculated at day 37.

ΔTGD: Tumor growth delay of treated animals—Tumor growth delay of control animals.

TABLE 2

Antitumor Activity of A2 on human colon carcinoma (HT29) in comparison with (2d).

| Compound | Treatment schedule | Dose mg/kg | Total Dose mg/kg | TI % 37$^{th}$ day | Tox | ΔTGD (0.5 g) days |
|---|---|---|---|---|---|---|
| A2 | iv q4dx8 | 12 | 80 | 78 | 0/7 | 0 |
|  | iv q4dx8 | 20 | 160 | 91 | 0/7 | 21 |
|  | iv q4dx8 | 40 | 320 | 98 | 0/7 | 56 |
| 2d | iv q4dx6 | 20 | 120 | 97 | 1/7 | 50 |

Tumor fragments were implanted sc. Treatment started when tumor was palpable.

TI % (tumor inhibition %) was calculated at day 37.

ΔTGD: Tumor growth delay of treated animals—Tumor growth delay of control animals.

TABLE 3

Antitumor activity of A1 against MX1, human mammary ca., in comparison with camptothecin (2a).

| Compound | treatment schedule | dose/ total dose mg/kg | TI % | Tox | ΔTGD (0.5 g) days | Tumor free |
|---|---|---|---|---|---|---|
| A1 | iv q4dx6 | 20/120 | 100 | 0/8 | >88 | 8/8 |
| 2a | iv q4dx4 | 10/40 | 100 | 3/8 | 69 | 0/8 |

Tumor fragments were implanted sc., treatment started when tumors were palpable.

Doses are expressed as camptothecin equivalents.

TI %: Inhibition of tumor growth 1 week after the last treatment

Tox: Number mice died for toxicity/total number mice

ΔTGD: Tumor growth delay treated. Tumor growth delay control

Tumor Free: cured mice at day 90 after tumor implant

TABLE 4

Antitumor activity of A1 against A2780, human ovaric ca., in comparison with camptothecin (2a).

| Compound | treatment schedule | dose/ total dose mg/kg | TI % | Tox | ΔTGD (0.5 g) days | Tumor free |
|---|---|---|---|---|---|---|
| A1 | iv q4dx6 | 15/90 | 100 | 0/7 | >82 | 7/7 |
|    | iv q4dx6 | 20/120 | 100 | 0/7 | >82 | 7/7 |
| 2A | iv q4dx3 | 10/30 | nd | 7/7 | nd | 0/7 |

Tumor fragments were implanted sc., treatment started when tumors were palpable.
  Doses are expressed as camptothecin equivalents.
  TI %: Inhibition of tumor growth 1 week after the last treatment
  Tox: Number mice died for toxicity/total number mice
  ΔTGD: Tumor growth delay treated. Tumor growth delay control
  Tumor Free: cured mice at day 90 after tumor implant

TABLE 5

Antitumor activity of A1 against M14, human melanoma., in comparison with camptothecin (2a).

| Compound | treatment schedule | dose/ total dose mg/kg | TI % | Tox | ΔTGD (0.5 g) days | Tumor free |
|---|---|---|---|---|---|---|
| A1 | iv q4dx6 | 15/90 | 100 | 0/7 | >78 | 7/7 |
|    | iv q4dx6 | 20/120 | 100 | 0/7 | >78 | 7/7 |
| 2a | iv q4dx6 | 10/60 | 94 | 0/7 | 34 | 0/7 |

Tumor fragments were implanted sc., treatment started when tumors were palpable.
  Doses are expressed as camptothecin equivalents.
  TI %: Inhibition of tumor growth 1 week after the last treatment
  Tox: Number mice died for toxicity/total number mice
  ΔTGD: Tumor growth delay treated. Tumor growth delay control
  Tumor Free: cured mice at day 90 after tumor implant

TABLE 6

Antitumor activity of A1 against A549, hunian NSC lung ca., in comparison with camptothecin (2a).

| Compound | treatment schedule | dose/ total dose mg/kg | TI % | Tox | ΔTGD (0.5 g) days | Tumor free |
|---|---|---|---|---|---|---|
| A1 | iv q4dx6 | 15/90 | 92 | 0/7 | >48 | 0/7 |
|    | iv q4dx6 | 20/120 | 94 | 0/7 | >70 | 0/7 |
| 2a | iv q4dx6 | 10/60 | 89 | 0/7 | 4 | 0/7 |

Tumor fragments were implanted sc., treatment started when tumors were palpable.
  Doses are expressed as camptothecin equivalents.
  TI %: Inhibition of tumor growth 1 week after the last treatment
  Tox: Number mice died for toxicity/total number mice
  ΔTGD: Tumor growth delay treated. Tumor growth delay control
  Tumor Free: cured mice at day 90 after tumor implant Therefore, the compounds of the present invention are useful in the treatment of leukemia and solid tumors, such as colon, colo-rectal, gastric, ovarian, mammary, prostate. lung, kidney and also melanoma tumors. A human can therefore be treated by a method comprising administering thereto a therapeutically effective amount of a polymeric conjugate of the invention. The condition of the human patient can thus be improved. The dosage range adopted will depend on the route of administration and on the age, weight and condition of the patient being treated. The polymeric conjugates of formula (1) are typically administered by parenteral route, for example intramuscularly, intravenously or by bolus infusion. A suitable dose range is from 1 to 1000 mg of camptothecin equivalent per $m^2$ body surface area, for instance from 10 to 100 $mg/m^2$.

The polymeric conjugate (1) may be formulated into a pharmaceutical composition together with a pharmaceutically carrier or diluent. Typically they are formulated for parenteral administration, for example by dissolution in water for injection or physiological saline.

The following Examples illustrate the invention.

EXAMPLE 1

Preparation of: N-(tert-butyloxycarbonyl)-6-aminohexanoyl-glycyl p-nitrophenyl-ester

[10a: n=5, $R_9$=Boc, P=p-nitrophenol]

Glycine ethyl ester hydrochloride (9.55g, 68.4 mmol), dissolved with dimethylformamide (100 ml), was added with triethylamine (9.5 ml, 68.4 mmol) and then with N-(tert-butyloxy carbonyl)-6-aminohexanoyl p-nitrophenyl-ester (19 g, 54 mmol), prepared following the same procedure described in our E.P. N°0673258. The reaction mixture was kept for two hours at room temperature, then the solvent was removed under reduced pressure. The residue was dissolved with ethyl acetate (300 ml) and washed in sequence with cold 1N aqueous hydrochloric acid (3×200 ml), water (100 ml), 5% aqueous solution of sodium hydrogen carbonate (2×200 ml) and water (2×200 ml). The organic phase was dried over anhydrous sodium sulphate, then the solvent was removed under reduced pressure. The residue was crystallized from ethyl ether to give N-(tert-butyloxycarbonyl)-6-aminohexanoyl-glycyl ethyl ester (15 g; TLC on Kieselgel plate $F_{254}$ (Merck), eluting system ethyl ether, $R_f$=0.3) which was suspended with ethanol (150ml) and treated under stirring with 1N aqueous sodium hydroxide (48 ml, 48 mmol). After one hour the reaction was added with 1N aqueous hydrochloric acid (48 ml 48 mmol) and distilled under reduced pressure. The residue was suspended with dry tctrahydrofurane (200 ml), added with p-nitrophenol (6,53g, 47 mmol), cooled at 0° C. and then added with a solution of 1,3-dicyclohexyl-carbodiimide (9.7 g, 47 mmol) in tetrahydrofurane (100 ml). The reaction was left to stand in the same conditions overnight, then filtered on a sintered glass funnel. The solvent was removed under reduced pressure. The residue was crystallized from ethyl ether to give 17.5 g of the title compound (10a). TLC on Kieselgel plate $F_{254}$ (Merck), eluting system methylene chloride/methanol (95/5 v/v) $R_f$=0.34.

$^1$H-NMR (200 MHz, DMSO) δ: 1.34 (s, 9H, t-Bu); 1.0–1.7 [m, 6H, NH—CH$_2$—(C$\underline{H}_2$)$_3$—CH$_2$13 CO]; 2.15 (t, J=7.2 Hz, 2H, NH—(CH$_2$)$_4$—CO); 2.85 [q, J=6.5 Hz, 2H, NH—C$\underline{H}_2$—(CH$_2$)$_4$—CO]; 4.11 (d, J=5.5 Hz, 2H, CONH C$\underline{H}_2$COO); 6.70 [bs, 1H, $\underline{NH}$—(CH$_2$)$_5$—CO]; 7.40 (m, 2H, aromatic 2,6-H); 8.30 (m, 2H, aromatic 3,5-H); 8.43 (t, J=5.5 Hz, 1H. CO$\underline{NH}$CH$_2$COO).

EXAMPLE 2

Preparation of: 20-O-[(N-tert-butyloxycarbonyl)-6-aminohexanoyl-glycyl]camptothecin

[11a: n=5, R$_9$=t-Boc, OCPT=(2a)]

Camptothecin (2a; 3.4 g, 10 mmol), suspended with dimethylsulfoxide (50 ml), was treated with N-(tert-butyloxycarbonyl)-6-aminohexanoyl-glycyl p-nitrophenyl-ester (10a; 6.3 g, 15 mmol) and 4-dimethylaminopyridine (2.4 g, 20 mmol). The reaction mixture was left to stand for 24 hours and then an addition aliquot of N-(tert-butyloxycarbonyl)-6-amino hexanoyl-glycyl p-nitrophenyl-ester (6.3 g, 15 mmol) was added. After 48 hours the reaction mixture was diluted with methylene chloride (500 ml) and washed with 0.2N aqueous hydrochloric acid (2×250 ml) and water (2×250 ml). The organic phase was dried over anhydrous sodium sulphate, then the solvent was removed under reduced pressure. The residue was dissolved with methylene chloride (100 ml), added with ethyl ether (500 ml) and kept at 0° C. overnight to give 5 g of the title compound (11a) in the solid form. TLC on Kieselgel plate F$_{254}$ (Merck), eluting system methylene chloride/methanol (95/5 v/v) R$_f$=0.44.

EXAMPLE 3

Preparation of: 20-O-(6-aminohexanoyl-glycyl)camptothecin

[6a: n=5, OCPT=(2a)]

20-O-[(N-tert-butyloxycarbonyl)-6-aminohexanoyl-glycyl]camptothecin (11a, 5 g) was treated with 90% aqueous trifluoroacetic acid (40 ml) for one hour, then the solvent was removed under reduced pressure. The residue was triturated with ethyl ether 300 ml) and filtered off. The solid was dissolved in methanol (200 ml), reduced to small volume (50 ml) under reduced pressure, added with ethyl ether (300 ml). The precipitate was collected to give 3.9 g of the title compound (6a).

TLC on Kieselgel plate F$_{254}$ (Merck), eluting system methylene chloride/methanol/acetic acid/water (80/20/7/3 v/v), R$_f$=0.83.

EXAMPLE 4

Preparation of: 20-O-[methacryloyl-glycyl-(6-aminohexanoyl-glycyl]camptothecin

[9a: n=5, OCPT=(2a)]

20-O-(6-aminohexanoyl-glycyl)camptothecin trifluoroacetate (6a; 2.53 g, 4mmol) was dissolved with anhydrous dimethylsulfoxide (10 ml) and added with methacryloyl-glycyl p-nitrophenyl ester (1.32 g, 5 mmol), prepared as described in Makromol.Chem. 178, 2159 (1977), and triethylamine (0.56 ml, 4 mmol). After standing overnight at room temperature, the solution was poured into water (100 ml) and the precipitate was collected and washed with water (2×100 ml). The solid material was flash chromatographed on silica gel using as eluting system a mixture of methylene chloride/ethanol (95/5 v/v) to give 2.2 g of the title compound (9a). TLC on Kieselgel plate F$_{254}$ (Merck), eluting system methylene chloride/methanol (9/1 v/v) R$_f$=0.62.

$^1$H-NMR (200 MHz, DMSO) δ: 0.90 (t, J=7.3 Hz, 3H, C$\underline{H}_3$-18); 1.1–1.6 [m, 6H, NHCH$_2$—(C$\underline{H}_2$)$_3$—CH$_2$CO]; 2.0–2.2 [m, 4H, C$\underline{H}_2$-19+NH—(CH$_2$)$_4$—C$\underline{H}_2$—CO]; 2.95 (q, J=6.3 Hz, 2H, NH—C$\underline{H}_2$—(CH$_2$)$_4$CO): 3.63 (d, J=5.8 Hz, 2H, CONH—C$\underline{H}$2-CONH); 3.97 (dd, J=17.8, 5.9 Hz, 1H, CONHC$\underline{H}_a$CH$_b$COO); 4.15 (dd, J=17.8, 5.9 Hz, 1H, CONHCH$_a$C$\underline{H}_b$COO), 5.29 (s, 2H, C$\underline{H}_2$-5); 5.33 [q, J=1.6 Hz, 1H, CH$_3$CH=C(H$_a$)(H$_b$)]; 5.48 (s, 2H, C$\underline{H}_2$-17); 5.69 [m, 1H, CH$_3$CH=C(Ha)(H$_b$)]; 7.15 (s, 1H, H-14); 7.6–7.9 (m, 3H, H-10+$\underline{H}$—11+$\underline{NH}$—(CH$_2$)$_5$CO]; 8.0 (t, J=5.8 Hz, 1H, CO—$\underline{NH}$—CH$_2$CONH); 8.15 (m, 2H, $\underline{H}$-9+$\underline{H}$-12); 8.32 (t, J=5.9 Hz, 1H, CO—NH—CH$_a$CH$_b$COO); 8.69 (s, 1H, $\underline{H}$-7).

EXAMPLE 5

Preparation of: 7-ethyl-10-hydroxy-20-O-(6-aminohexanoyl-glycyl)camptothecin trifluoro acetate [6b: n=5, OCPT=(2d)]

7-ethyl-10-hydroxy-camptothecin (2d, 0.8 g, 2mmol). N-(tert-butoxycarbonyl)-6-amino-hexanonyl-glycyl p-nitrophenylester (10a; 2.5g, 6 mmol) and 4-dimethylaminopyridine were dissolved with dry dimethylsulfoxide (30 ml) and kept at room temperature for 3 days under stirring. After that the reaction mixture was poured in 0.1N aqueous hydrochloric acid (500 ml) to give a precipitate which was collected, then dissolved in methylene chloride (300 ml) and washed with water (2×100 ml). The organic phase was separated, dried over anhydrous sodium sulfate and evaporated under reduced pressure. The residue was treated with 90% aqueous trifluoroacetic acid (40 ml) for three hours then the solvent was removed under reduced pressure and the residue was flash chromatographed on silica gel using a mixture of methylene chloride/acetic acid/methanol (100/5/20 v/v) as eluting system. Fractions containing the title compound were pooled and evaporated under reduced pressure to give 1.02 g of (6b) as trifluoroacetate salt derivative. TLC on Kieselgel plate F$_{254}$ (Merck), eluting system methylene chloride/methanol/acetic acid/water (80/20/7/3 v/v), R$_f$=0.4.

$^1$H-NMR (200 MHz, DMSO) δ: 0.89 (t, J=7.2 Hz, 3H, C$\underline{H}_3$—CH$_2$—20); 1.1–1.5 (m, 9H, NH$_2$—CH$_2$—C$\underline{H}_2$—CH$_2$—C$\underline{H}_2$—CH$_2$+C$\underline{H}_3$—CH$_2$—7); 1.80 (s, 3H, C$\underline{H}_3$—COOH); 2.10 (m, 4H, CH$_3$—C$\underline{H}_2$—20+ C$\underline{H}_2$—CONH); 2.53 (t, 6.8 Hz, 2H, C$\underline{H}_2$—NH$_2$); 3.06 (m, 2H, CH$_3$—C$\underline{H}_2$—7); 3.98, 4.13 (two-dd, J=17.6, 5.7 Hz, 2H, CONH—C$\underline{H}_2$—CO); 5.27 (s, 2H, C$\underline{H}_2$—5); 5.46 (s, 2H, C$\underline{H}_2$—17) 7.01 (s, 1H, $\underline{H}$-14); 7.40 (m, 2H, $\underline{H}$-9+$\underline{H}$-11); 7.99 (d, J=9.8 Hz, 1H, $\underline{H}$—12); 8.33 (t, J=5.7 Hz. 1H, CONH—CH$_2$—CO).

EXAMPLE 6

Preparation of: 7-ethyl-10-hydroxy-20-O-(6-aminohexanoyl-glycyl)camptothecin hydrochloride

[6b: n=5, OCPT=(2d)]

7-ethyl-10-hydroxy-camptothecin (2d, 0.8 g, 2 mmol) was reacted with N-(tert-butoxycarbonyl)-6-aminohexanonyl-glycyl p-nitrophenylester (10a; 2.5 g, 6 mmol) and 4-dimethyl amino pyridine as described in Example 5. The crude material, obtained from the reaction mixture by methylene chloride extraction, was dissolved in a mixture of 1.5N hydrochloric acid and acetic acid (20 ml). After standing for one hour under stirring at room temperature, the solution was reduced to small volume by distillation and ethyl ether (100 ml) was added. The precipitate was collected and washed with ethyl ether (2×50 ml) to give 1 g of the title compound (6b) as free amino derivative.

EXAMPLE 7

Preparation of MAG-camptothecin via Route I
[A1: n=5, OCPT=(2a)]

Polymeric precursor B (R$_2$=p-nitrophenyloxy, 2.58 g, containing 1.16×10$^3$ eq. of p-nitro phenyl ester residue), prepared as described in Makromol.Chem.178, 2159 (1977), was dissolved with dry dimethylsulfoxide (15ml) and added with 20-O-(6-aminohexanoyl-glycyl) camptothecin trifluoroacetate (6a; 0.63 g, 1 mmol), followed by triethylamine (0.14 ml, 1 mmol). The reaction mixture was kept at room temperature for 22 hours under stirring, then 2-propanolamine (0.05 ml) was added and the mixture left under stirring for one more hour. After that, the reaction mixture was precipitated with ethyl acetate (200 ml) and left under stirring for 30 min. The solid material was collected on a sintered glass funnel, washed with ethyl acetate (200 ml) and ethyl ether (100 ml) and then dissolved with ethanol (30 ml). The alcoholic solution was treated with wet DOWEX-50, sulphonic form, (1.2 g) under stirring for 30 min. and, after that, was added dropwise to n-hexane (200 ml). The precipitate was collected on a sintered glass funnel, washed with ethyl ether and dried to constant weight to give 2.68 g of the title compound (A1). Weight-average molecular weight (Mw): 19.800. Polydispersity (Mw/Mn): 1.5. Content of camptothecin, determined after alkaline hydrolysis, 10% w/w.

EXAMPLE 8

Preparation of MAG-(7-ethyl-10-hydroxycamptothecin) via Route I
[A2: n=5, OCPT=(2d)]

Polymeric precursor (B) ($R_2$=p-nitrophenyloxy, 2.58 g, containing $1.6 \times 10^{-3}$ eq. of p-nitro phenyl ester residue), prepared as described in Makromol.Chem.178, 2159 (1977), was dissolved with dry dimethylsulfoxide (15 ml) and added with 7-ethyl-10-hydroxy-20-O-(6-aminohexanoyl-glycyl) camptothecin trifluoro acetate (6b; 0.68 g. 1 mmol), followed by triethylamine (0.14 ml, 1 mmol). The reaction mixture was kept at room temperature for 22 hours under stirring, then 2-propanolamine (0.05 ml) was added and the mixture left under stirring for one more hour. After that, the reaction mixture was precipitated with ethyl acetate (200 ml) and left under stirring for 30 min. The solid material was collected on a sintered glass funnel, washed with ethyl acetate (200 ml) and ethyl ether (100 ml) and then dissolved with ethanol (30 ml). The alcoholic solution was treated with wet DOWEX-50, sulphonic form, (1.2 g) under stirring for 30 min. and, after that, was added dropwise to n-hexane (200 ml). The precipitate was collected on a sintered glass funnel, washed with ethyl ether and dried to constant weight to give 2.68 g of the title compound [A2] Weight-average molecular weight (Mw): 20.500.

Polydispersity (Mw/Mn): 1.87. Content of 7-ethyl-10-hydroxy-camptothecin, determined after alkaline hydrolysis, 10% w/w.

EXAMPLE 9

Preparation of MAG-camptothecin via Route II
[A1: n=5, OCPT=(2a)]

20-O-[methacryloyl-glycyl-(6-aminohexanoyl)-glycyl] camptothecin (9a: 1.26g, 2 mmol), N-(2-hydroxypropyl) methacrylamide (8, 4.4 g, 31 mmol), prepared as described in Makromol. Chem.178, 2159 (1977), and 2,2'-azobisisobutyronitrile (0.26 g, 1.6 mmol) were dissolved with anhydrous dimethysulfoxide (20 ml), kept at 60° C. under nitrogen and stirred for 24 hours. After that, the reaction mixture was cooled at room temperature and poured into ethyl acetate (500 ml). The precipitate is collected and dissolved with ethanol (50 ml) from which is re-precipitated by adding ethyl acetate (500 ml). The solid is collected, washed with ethyl acetate ethyl ether (2×100 ml) to give 5 g of the title compound (A1).

What is claimed is:

1. A polymeric conjugate which consists of:

(i) from 85 to 97 mol % of N-(2-hydroxypropyl) methacryloylamide units represented by formula (3)

(3)

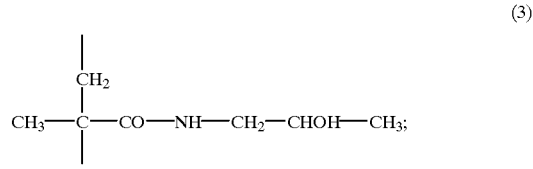

(ii) from 3 to 15 mol % of 20-O-(N-methacryloyl-glycyl-aminoacyl-glycyl)camptothecin units represented by formula (4)

(4)

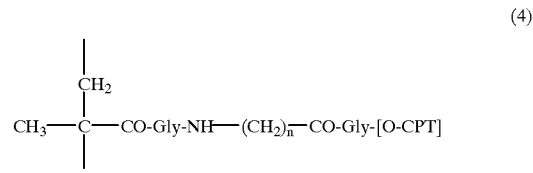

wherein n is from 2 to 8, —[O-CPT] represents the residue of a camptothecin of formula (2)

(2)

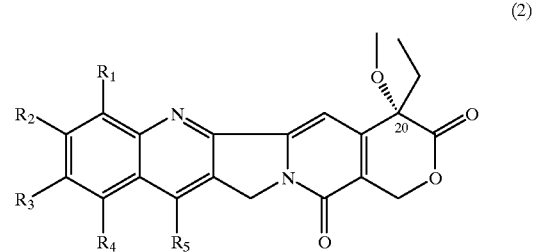

which is linked at the C-20 position and in which each of $R_1$, $R_2$, $R_3$, $R_4$ and $R_5$, which are the same or different, is hydrogen, $C_1$–$C_{12}$ linear or branched alkyl, nitro, amino, $(CH_2)_a NR_6 R_7$ in which a is from 0 to 4 and $R_6$ and $R_7$ are hydrogen or one of $R_6$ or $R_7$ is hydrogen and the other of $R_6$ or $R_7$ is $C_1$–$C_6$ alkyl, or $NR_6 R_7$ represents a piperazino or N-alkyl-piperazino ring optionally substituted with $C_1$–$C_6$ linear or branched alkyl, or a piperidino ring, $(CH_2)_a NHCOR_8$ in which a is as above defined and $R_8$ is $C_1$–$C_8$ linear or branched alkyl or a group $NR_6 R_7$ as above, hydroxy or O—CO—$R_8$ in which $R_8$ is as above defined or represents a 1-piperidino ring or 1,4'-bipiperidine, or $R_2$ and $R_3$ taken together represent the residue O—$(CH_2)_b$—O, in which b is 1 or 2, or $R_4$ and $R_5$ represent the residue $(CH_2)_m$, in which m is from 2 to 4, or the residue $CH_2$—O—$CH_2$ or $CH_2 NHCH_2$ and (iii) from 0 to 12 mol % of N-methacryloyl-glycine or N-(2-hydroxypropyl)methacryloyl-glycinamide units represented by formula (5)

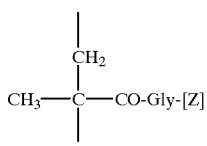
(5)

wherein [Z] represents a hydroxy group or a residue of formula —NH—CH$_2$—CH(OH)—CH$_3$.

2. A polymeric conjugate according to claim 1 which contains the N-(2-hydroxypropyl)methacryloylamide units represented by the formula (3) in a molar proportion of 90%.

3. A polymeric conjugate according to claim 1 which contains 10 mol % of the units represented by the formula (4).

4. A polymeric conjugate according to claim 1 wherein the unit of formula (5) is absent.

5. A polymeric conjugate according to claim 1 in which —[O-CPT] in formula (4) is a residue of a camptothecin of formula (2) selected from: camptothecin, 9-aminocamptothecin, 9-nitrocamptothecin, 7-ethyl-10-hydroxy-camptothecin, 7-ethyl-10-[1,4'-bipiperidinyl] carbonyloxycamptothecin, 7-methylendimethylamino-10-hydroxycamptothecin and 7-[methylene-(4'-methylpiperazino)]-9,10-ethylendioxycamptothecin.

6. A polymeric conjugate according to claim 1 in which the content of active camptothecin derivative of formula (2) is 10% (w/w).

7. A process for producing a polymeric conjugate as defined in claim 1, which process comprises reacting a 20-O-(aminoacyl-glycyl)camptothecin derivative of formula (6)

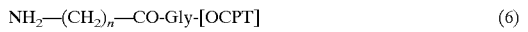
(6)

wherein n and [O-CPT] are as defined in claim 1, with a polymer (B) consisting essentially of:

from 85 to 97 mol % of N-(2-hydroxypropyl) methacryloylamide units represented by formula (3) as defined in claim 1, and from 3 to 15 mol % of N-methacryloyl-glycyl derivative units represented by formula (7)

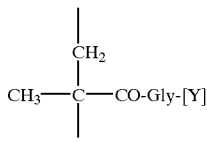
(7)

wherein [Y] is the residue of an active ester or a hydroxy group;

and optionally displacing the remaining active ester groups with 1-amino-2-propanol.

8. A process for producing a polymeric conjugate as defined in claim 1, which process comprises the polymerization between N-(2-hydroxypropyl)methacrylamide of the formula (8)

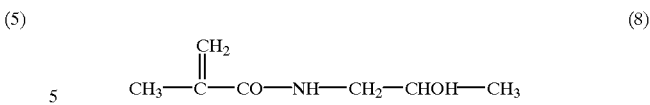
(8)

and 20-O-[methacryloyl-glycyl-(aminoacyl)-glycyl] camptothecin derivatives of the formula (9)

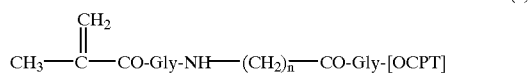
(9)

wherein n and [OCPT] are as defined in claim 1, in conditions capable of preserving the nature of linkage between camptothecin and spacer glycyl-aminoacyl-glycyl as well as that of the conjugate.

9. A 20-O-acylamino-glycyl-camptothecin derivative of the formula (6) as defined in claim 7 or a salt thereof.

10. A process for producing a compound of the formula (6) as defined in claim 7, which process comprises condensing a derivative of formula (2) as defined above with a N-protected aminoacyl-glycyl derivative of formula (10):

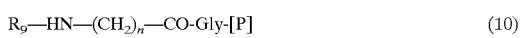
(10)

wherein n is as defined above, R$_9$ represents an amino-protecting group and [P] is a residue of an activated ester, to give a compound represented by formula (11):

(11)

wherein n and R$_9$ are as defined above and [OCPT] is as defined above; and removing the N-protecting group from the resulting compound.

11. A 20-O-[methacryloyl-glycyl-(aminoacyl)-glycyl] camptothecin derivative of the formula (9) as defined in claim 8 or a salt thereof.

12. A process for producing a derivative of the formula (9) as defined in claim 11 which process comprises condensing a camptothecin derivative of the formula (6) as defined above with N-methacryloyl-glycyl of formula (7'),

(7')

wherein [Y'] is a leaving group.

13. A pharmaceutical composition comprising a pharmaceutically acceptable diluent or carrier and, as active ingredient, a polymeric conjugate as defined in claim 1.

14. A polymeric conjugate according to claim 1 which is MAG-camptothecin, in which the camptothecin content is 10% (w/w).

15. A polymeric conjugate according to claim 1 which is obtainable by reacting a 20-O-(6-aminohexanoyl-glycyl) camptothecin derivative of formula (6)

(6)

wherein [O-CPT] is the residue of camptothecin, with a polymer (B) consisting essentially of: from 85 to 97 mol % of N-(2-hydroxypropyl)methacryloylamide units represented by formula (3) as defined in claim 1, and from 3 to 15 mol % of N-methacryloyl-glycyl derivative units represented by formula (7)

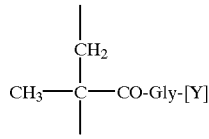
(7)

wherein [Y] is p-nitrophenoxy group; and optionally displacing the remaining active ester groups with 1-amino-2-propanol.

16. A polymeric conjugate according to claim 1 which is obtainable by the polymerization between N-(2-hydroxypropyl)methacrylamide of the formula (8)

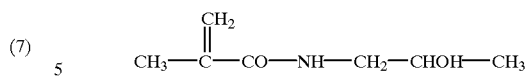
(8)

and 20-O-[methacryloyl-glycyl-(6-aminohexanoyl)-glycyl] camptothecin derivatives of the formula (9)

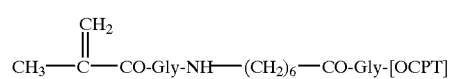
(9)

wherein [OCPT] is the residue of camptothecin.

17. A pharmaceutical composition comprising a pharmaceutically acceptable diluent or carrier and, as active ingredient, a polymeric conjugate as defined in claim 1.

* * * * *